United States Patent [19]

Hubele et al.

[11] 4,063,921
[45] Dec. 20, 1977

[54] METHOD FOR THE CULTIVATION OF PLANTS EMPLOYING α-CYANO-α-HYDROXYIMINO-ACETAMIDE DERIVATIVES

[75] Inventors: Adolf Hubele, Magden; Manfred Kühne, Pfeffingen, both of Switzerland

[73] Assignee: Ciba-Geigy Corporation, Ardsley, N.Y.

[21] Appl. No.: 718,446

[22] Filed: Aug. 26, 1976

Related U.S. Application Data

[63] Continuation-in-part of Ser. No. 404,548, Oct. 9, 1973, abandoned.

[51] Int. Cl.$^2$ ............................................. A01N 9/20
[52] U.S. Cl. ........................................... 71/76; 71/105
[58] Field of Search ........................... 71/105, 118, 76

[56] References Cited

U.S. PATENT DOCUMENTS

| | | | |
|---|---|---|---|
| 3,625,987 | 12/1971 | Hubele | 71/105 X |
| 3,923,491 | 12/1975 | O'Brien et al. | 71/118 X |

Primary Examiner—Lewis Gotts
Assistant Examiner—Catherine L. Mills
Attorney, Agent, or Firm—Harry Falber

[57] ABSTRACT

The invention relates to a method for the cultivation of plants involving the regulation of their growth which comprises applying an effective amount of a compound of the formula I

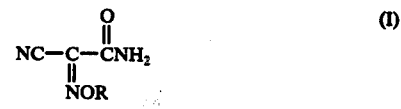

wherein R represents hydrogen or a sodium, potassium or calcium ion.

5 Claims, No Drawings

METHOD FOR THE CULTIVATION OF PLANTS EMPLOYING α-CYANO-α-HYDROXYIMINO-ACETAMIDE DERIVATIVES

CROSS REFERENCE

This application is a continuation-in-part of our application Ser. No. 404,548 filed Oct. 9, 1973, now abandoned.

DETAILED DISCLOSURE

The present invention relates to a method for the regulation of plant growth employing α-cyano-α-hydroxyimino-acetamide derivatives.

More particularly the present invention relates to a method for regulation of plant growth which comprises applying to plants under cultivation an effective amount of a compound of the formula I

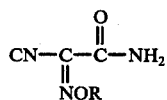

wherein R represents hydrogen or a sodium, potassium or calcium ion.

Especially preferred for use in the method of the invention are compounds of the formula I wherein R represents hydrogen or a sodium ion.

The compounds of the formula I may be prepared analogously to known methods for example as follows:

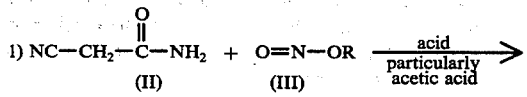

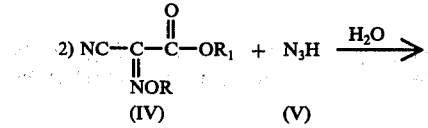

whereby in formulae II to V, the symbol R has the meanings given for formula I, and $R_2$ represents an alkyl group, preferably a methyl group.

Salts that are formed in the course of the process of preparation of the active substances can be converted by acidification into the free oxime, or by salt formation directly into other salts. The free oxime can be converted by the usual methods into a desired salt, e.g. by addition of a metal hydroxide solution or metal salt solution.

The following examples serve to further illustrate the preparation of the compounds of the invention. Temperatures are expressed in degrees Centigrade.

PREPARATIVE EXAMPLE

Preparation of the Sodium Salt of α-Cyano-α-hydroxyimino-acetamide 85 g of cyanoacetamide and 85 g of sodium nitrite are suspended in 350 ml of water. 120 g of glacial acetic acid are added dropwise to this solution, and the reaction mixture is then stirred for 18 hours at room temperature. The suspension obtained is concentrated by evaporation to a third of its volume, cooled and then filtered. The substance filtered off (consisting of 61% of sodium salt and 39% of free oxime) is dissolved in warm water, and the calculated amount (160 ml) of a 10% aqueous NaOH-solution added to the solution. This reaction mixture is concentrated, mixed with ethanol, filtered, and the filtered substance washed with ethanol.

The dried final product

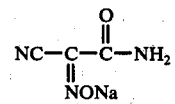

melts at 298° (decomposition) (compound No. 1).

Acidification of this product produces the free oxime:

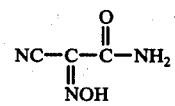

which melts at 183° (decomposition) (compound No. 2).

The following compounds are obtained in an analogous manner:

| Compound No. | R | n | Physical Data |
|---|---|---|---|
| 1 | Na | 1 | m.p. 298° (decomposition) |
| 2 | H | — | m.p. 183° (decomposition) |
| 3 | Ca | 2 | m.p. 340° |
| 4 | K | 1 | m.p. 265° (decomposition) |

In accordance with the present invention it has now surprisingly been found that the growth of plants may be advantageously controlled or modified by the application of the compounds of the formula I.

In particular the compounds of the formula I have been found to restrict vegetative growth and/or growth in height in a variety of plant species, both mono- and di-cotyledenous such as for example grasses, cereal, crops, ornamental plants, leguminosae and other cultures. The compounds of the formula I are particarly suited for inhibiting and or regulating the growth of grasses, cereal crops and soyabean plants.

In the case of grasses, the application of the compounds of the formula I results in a slower rate of growth, so that, e.g., lawns, golf-courses and green shoulders along motor-ways and turnpikes will require less frequent cutting. The economic advantages accrueing are self-evident.

With cereal crops application of the active substances results in the development of shorter sturdier stems and a concommitant improvement in fruit development.

The effect of growth inhibition in ornamental plants and ornamental shrubs is that they develop as strong, smaller plants of greater uniformity. Moverever ornamental plants normally growing to a substantial height can, by treatment with the compounds of the formula I, be cultivated as compact pot-plants.

Of these various forms of plant growth regulation the most interesting aspects for the purposes of the present invention have been found to be 1. The diminution and control of vegetative growth in grasses and cereal crops and
2. The diminution and control of vegetative growth in soyabean plants.

1. CONTROL OF VEGETATIVE GROWTH IN GRASSES AND CEREAL CROPS

The compounds of the formula I can be used in the control and in particular retardation of growth in grasses. One of the benefits of this reduced growth in for example, lawns, sports fields and other grassed-over areas is the saving in manure and/or fertilizer and in the case of the latter the reduced frequency at which they must be mown or scythed. The prime importance of this property becomes clear when grasses on roadsides, river and canal banks, airports and the like are considered. Under normal circumstances such areas require regular mowing or scything which involves high labour and machinery costs. In addition the danger to the personel working for example beside highways and in airports is considerable.

In cereal crops the primary effect achieved by the compounds of the formula I is a reduction in plant size especially height of growth. As a direct result of the reduction in height the plant gains in sturdiness, the leaves and stems grow stronger and in the case of cereals a reduction of the internodal distance results in greater resistance to bending and breaking.

The following test illustrates the effectiveness of the compounds of the invention in regulating the growth of grasses

EXAMPLE 1

Growth Inhibition in Grasses (Postemergence Method)

Seeds of the grasses Lolium perenne, Poa pratensis, Festuca ovina, and Dactylis glomerata were sown in plastic dishes filled with an earth/turf/sand mixture. After 20 days the germinated grasses were cut back to a height of 4 cm above the soil and 2 days later sprayed with aqueous spray broths of the active substance.

The amount of active substance corresponded to a rate of application of 5 kg of active substance per hectare. 21 days after application the growth of the grasses was evaluated according to the following linear rating:

1 = strong inhibition (no growth from the time of application)

9 = no inhibition (growth as untreated control)

The following results were obtained.

| Compound | Lolium perenne | Poa pratensis | Festuca ovina | Dactylis glomerata |
|---|---|---|---|---|
| 1 | 5 | 4 | 3 | 4 |
| 2 | 6 | 3 | 2 | 2 |

2. CONTROL OF VEGETATIVE GROWTH IN SOYABEAN PLANTS

In accordance with a further aspect of the present invention it has been found that the application of compounds of the formula I as described above results in marked reduction in vegetative growth in soyabean plants. As a direct consequence of this growth inhibition it is possible to sow the soya bean plants with less space between individual rows of plants. This results in a substantial saving of space and a consequential increase in crop yield per unit of cultivated ground.

Furthermore the treated plants have been found to develop stronger, greener leaves than untreated control plants and to produce, in proportion to the foliage, an increased blossom and degree of fruit setting. The smaller size of the plants and the possibility of growing the plants closer together also provide better protection against flattening or other dammage by wind and rain.

The extent and mode of action will of course depend on the quantity of active substance applied, the time of application and the variety of plant treated as well as upon ambient conditions.

The following test illustrates the effectiveness of the compounds of the invention in the control of vegetative growth in soyabean plants.

EXAMPLE 2

Plots of soyabean plants of the variety "Wayne" each averaging 25 m$^2$ were sprayed in the 5–6 trifoliate leaf stage with aqueous preparations of the active substance to give application rates of 2.0 and 0.5 kg/hectare of active substance. Several plots were maintained as untreated controls.

The following Table gives the harvest yield in Bushels/Acre and as a percentage of the control harvest.

|  | kg AS/ha | Yield Bushels/Acre | % of Control |
|---|---|---|---|
| Control | — | 27.8 | 100 |
|  | 2 | 36.6 | 132 |
| Compound No. 2 | 0.5 | 32.0 | 115 |

The production of active substance compositions for use in the process of the present invention is carried out in a manner well known in the art by intimately mixing and/or grinding the active substances of the formula I with the suitable carriers, optionally with the addition of dispersants or solvents which are inert towards the active substance. The active substances may take and be used in the following forms:

Solid forms:
 dusts, tracking agents, granules, coated granules, impregnated granules, homogeneous granules and pellets Liquid forms:
 a. active substance concentrates which are dispersible in water, wettable powders, pastes, emulsions;
 b. solutions and aerosols To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

The particle size of the carriers for dusts is advantageously up to 0.1 mm, for tracking agents from about 0.075 to 0.2 mm, and for granules 0.2 mm or larger.

The solid forms contain the active substances in concentrations from 0.5% to 80%.

To these mixtures can also be added additives which stabilize the active substance and/or non-ionic, anionic and cationic surface active substances, which for example improve the adhesion of the active ingredients on plants or parts of plants (adhesive and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation product of urea and formaldehyde, and also latex products.

Preferred dispersions (suspensions and emulsions) are manufactured by mixing or grinding the active substance with carriers accompanied by the addition of dispersing agents and solvents, in the process of which there result firstly dispersible active substance concentrations, such as wettable powders and emulsifiable concentrates.

The water-dispersible concentrates of the active substances i.e. wettable powders, pastes and emulsifiable concentrates, are agents which can be diluted with water to any concentration desired. They consist of active substance, carrier, optionally additives which stabilize the active substances surface-active substances and anti-foam agents and, optionally, solvents. The active substance concentrations in these agents are from 5-80%.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammmonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salt of oleoyl methyl tauride, ditertiary acetylene glycols, dialkyl dilauryl ammonium chloride and fatty acid alkali and alkaline earth metal salts.

Suitable anti-foam agents are silicones.

The active substance is so mixed, ground sieved and strained with the additives mentioned above that, in wettable powders, the solid particle size of from 0.02 to 0.04 and in pastes, of 0.03 is not exeeded. To produce emulsifiable concentrates and pastes, dispersing agents such as those given in the previous paragraphs, organic solvents and water are used. Examples of suitable solvents are the following: alcohols, benzene, xylenes, toluene, dimethylsulphoxide, and mineral oil fractions boiling between 120 and 350° C. The solvents must be practically odorless, not phytotoxic, inert to the active substance and not readily inflammable.

Furthermore, the agents according to the invention can be applied in the form of solutions. For this purpose the active substances of formula I are dissolved in suitable organic solvents, mixtures of solvents or in water. Aliphatic and aromatic hydrocarbons, chlorinated derivatives thereof, alkyl naphthalenes and mineral oils singly or in admixture, can be used as organic solvents. The solutions contain the active substance in a concentration range from 1% to 20%.

In addition the agents described according to the invention can be mixed with other biocidally active substances or agents. Thus in order to broaden the activity spectrum the new agents may contain, for example, insecticides, fungicides, bactericides, fungistatics, bacteriostatics or nematocides, in addition to the cited active substances of the formula I. The agents according to the invention may also contain plant fertilisers, trace elements etc.

The active substances of the formula I can, for example, be formulated as follows. The parts denote parts by weight.

Granules

The following substances are used to manufacture 5% granules:
  5 parts of the sodium salt of α-cyano-α-hydroxyimino-acetamide
  15 parts of rosin
  80 parts of pumice-stone (particle size 0.2–0.6 mm)

The active substance and rosin are dissolved in methylene chloride. The resulting solution is sprayed on pumice-stone and then the solvent is evaporated in vacuo.

Wettable Powder

The following constituents are used to manufacture (a) a 70%, (b) a 25% and (c) a 10% wettable powder:

a.

70 parts of a compound of the formula I
  5 parts of sodium dibutylnaphthalene sulphonate,
  3 parts of naphthalenesulphonic acid/phenolsulphonic acid/formaldehyde condensate (3:2:1),
  20 parts of kaolin,
  22 parts of Champagne chalk;

b.

25 parts of α-cyano-α-hydroxyimino-acetamide
  5 parts of oleylmethyltaurid-sodium-salt,
  2.5 parts of naphthalenesulphonic acid/formaldehyde condensate,
  0.5 parts of carboxymethyl cellulose,
  5 parts of neutral potassium-aluminium-silicate,
  62 parts of kaolin;

c.

10 parts of a compound of the formula I
  3 parts of a mixture of the sodium salts of saturated fatty alcohol sulphates,
  5 parts of naphthalenesulphonic acid/formaldehyde condensate,
  82 parts of kaolin.

The indicated active substance is applied to the corresponding carriers (kaolin and chalk) and then these are mixed and ground, to yield wettable powders of excellent wettability and having an excellent capacity for forming suspensions. By diluting these wettable powders with the 10-fold amount of water it is possible to obtain suspensions containing 7%, 2,5% and 1% of active substance.

Paste

The following substances are used to manufacture a 45% paste:
- 45 parts of a compound of the formula I
- 5 parts of sodium aluminium silicate,
- 14 parts of cetyl polyglycol ether with 8 mols of ethylene oxide,
- 1 part of oleyl polyglycol ether with 5 mols of ethylene oxide,
- 2 parts of spindle oil,
- 10 parts of polyethylene glycol,
- 23 parts of water.

The active substance is intimately mixed with the addition in appropriate devices and ground. A paste is obtained from which, by diluting it with water, is possible to manufacture suspensions of every desired concentration.

Emulsion Concentrate

To manufacture a 25% emulsion concentrate
- 25 parts of a compound of the formula I
- 5 parts of a mixture of nonylphenolpolyoxyethoxyethylene and calcium dodecylbenzenesulphonate
- 35 parts of 3,5,6-trimethyl-2-cyclohexan-1-one,
- 35 parts of dimethyl formamide, are mixed together. This concentrate can be diluted with water to give emulsions in desired concentrations. Such aqueous emulsions can be used for regulating plant growth.

Application of the active substances as liquid preparations to the aereal portions of the plant is preferred, though application in other forms to the soil may be desirable in certain instances. For effective control of vegetative growth the active ingredient should be applied to the plant in an amount of from 0.05 to 5 (preferably 2) kg per hectare.

We claim:

1. A method for the cultivation of plants wherein the growth or development of the plants is inhibited, which method comprises applying to the plant or plants under cultivation an effective amount of a compound of the formula I

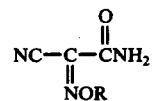

wherein R represents hydrogen or a sodium, potassium or calcium ion.

2. A method according to claim 1 wherein in the compound of the formula I

R represents hydrogen or a sodium ion.

3. A method according to claim 1 for the cultivation of grasses, cereal crops or soya bean plants wherein the vegetative growth of the plants is reduced which method comprises applying to the plant or plants under cultivation an effective amount of a compound of the formula I

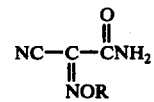

wherein R represents hydrogen or a sodium, potassium or calcium ion.

4. A method according to claim 3 wherein in the compound of the formula I R represents hydrogen or a sodium ion.

5. A method according to claim 4 for the cultivation of soya plants wherein vegetative growth is reduced, which method comprises applying to the soya bean plants an effective amount of α-cyano-α-hydroxyiminoacetamide of the formula

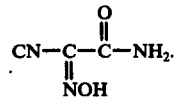

* * * * *